US008501701B2

(12) United States Patent
Yedgar et al.

(10) Patent No.: US 8,501,701 B2
(45) Date of Patent: *Aug. 6, 2013

(54) USE OF LIPID CONJUGATES IN THE TREATMENT OF DISEASE

(75) Inventors: Saul Yedgar, Jerusalem (IL); Moshe Ligumski, Jerusalem (IL); Miron Krimsky, Jerusalem (IL)

(73) Assignee: Yissum Research Development Company of the Hebrew University of Jerusalem Ltd. (IL)

( * ) Notice: Subject to any disclaimer, the term of this patent is extended or adjusted under 35 U.S.C. 154(b) by 273 days.

This patent is subject to a terminal disclaimer.

(21) Appl. No.: 11/598,812

(22) Filed: Nov. 14, 2006

(65) Prior Publication Data
US 2007/0117779 A1 May 24, 2007

Related U.S. Application Data

(63) Continuation-in-part of application No. 10/952,496, filed on Sep. 29, 2004, now Pat. No. 7,393,938, and a continuation-in-part of application No. 10/790,182, filed on Mar. 2, 2004, now Pat. No. 7,141,552, which is a continuation-in-part of application No. 09/756,765, filed on Jan. 10, 2001, now Pat. No. 7,034,006.

(60) Provisional application No. 60/174,907, filed on Jan. 10, 2000.

(51) Int. Cl.
A01N 43/04 (2006.01)
A61K 31/70 (2006.01)
A61K 31/715 (2006.01)
A61K 31/727 (2006.01)

(52) U.S. Cl.
USPC .......... 514/42; 514/53; 514/54; 514/56; 514/61; 514/62

(58) Field of Classification Search
USPC .............. 514/54, 56, 57, 78; 536/53
See application file for complete search history.

(56) References Cited

U.S. PATENT DOCUMENTS

| 4,604,376 A | 8/1986 | Teng |
| 4,624,919 A | 11/1986 | Kokusho |
| 4,654,327 A | 3/1987 | Teng |
| 5,064,817 A | 11/1991 | Yedgar et al. |
| 5,169,636 A | 12/1992 | Nanba et al. |
| 5,354,853 A | 10/1994 | Staveski |
| 5,401,511 A | 3/1995 | Margalit |
| 5,401,777 A | 3/1995 | Ammon et al. |
| 5,464,942 A | 11/1995 | Sakurai et al. |
| 5,470,578 A | 11/1995 | Aoki et al. |
| 5,512,671 A | 4/1996 | Piantadose |
| 5,587,363 A | 12/1996 | Henderson |
| 5,707,821 A | 1/1998 | Rydel et al. |
| 5,733,892 A | 3/1998 | Sakurai |
| 5,785,975 A | 7/1998 | Parikh |
| 6,022,866 A | 2/2000 | Falk et al. |
| 6,043,231 A | 3/2000 | Pruzanski et al. |
| 6,071,532 A | 6/2000 | Chaikof et al. |
| 6,162,787 A | 12/2000 | Sorgente et al. |
| 6,171,614 B1 | 1/2001 | Chaikof et al. |
| 6,180,596 B1 | 1/2001 | Tsao |
| 6,325,385 B1 | 12/2001 | Iwashita |
| 6,749,813 B1 | 6/2004 | David |
| 7,034,006 B2 * | 4/2006 | Yedgar et al. ............ 514/42 |
| 7,101,859 B2 | 9/2006 | Yedgar et al. |
| 7,141,552 B2 * | 11/2006 | Yedgar et al. ............ 514/44 |
| 7,393,938 B2 * | 7/2008 | Yedgar ................. 536/18.7 |
| 7,504,384 B2 | 3/2009 | Yedgar et al. |
| 7,608,598 B2 | 10/2009 | Yedgar |

FOREIGN PATENT DOCUMENTS

| EP | 0236951 | 9/1987 |
| EP | 0581282 B | 2/1994 |
| EP | 1046394 A | 10/2000 |
| JP | 04082893 | 3/1992 |
| JP | 09030970 | 2/1997 |
| JP | 09030979 | 2/1997 |
| JP | 2002345455 | 12/2002 |
| JP | 2003160498 | 3/2003 |
| JP | 2003335801 | 11/2003 |
| JP | 2004018841 | 1/2004 |
| JP | 2004170194 | 6/2004 |
| WO | WO 87/02777 | 5/1987 |
| WO | WO 91/00289 | 1/1991 |
| WO | WO 96/04001 | 2/1996 |
| WO | WO 96/11670 | 4/1996 |
| WO | WO 9628544 | 9/1996 |
| WO | WO 9701330 | 1/1997 |
| WO | WO 97/48337 | 12/1997 |
| WO | WO 9816198 | 4/1998 |

(Continued)

OTHER PUBLICATIONS

Kokotos, G. et al. J. Med. Chem. 2002, 45, 2891-2893.*
Cummings, B. S. Biochemical Pharmacology 74 (2007) 949-959.*
Ehehalt, R. Int. J. Mol. Sci. 2010, 11, 4149-4164.*
Albini, A, Iwamoto, Y, Kleinman, HK, Martin, GR, Aaronson, SA, Kozlowski, JM and McEwan, RN (1987) "A rapid in vitro assay for quantitating the invasive potential of tumor cells" *Cancer Res* 47(12):3239-45.
Balsinde, J, Balboa, MA, Yedgar, S and Dennis, EA (2000) "Group V phospholipase A(2)-mediated oleic acid mobilization in lipopolysaccharide-stimulated P388D(1) macrophages" *J Biol Chem* 275(7):4783-6.
Beck, G, Yard, BA, Schulte, J, Oberacker, R, Van Ackern, K, Van Der Woude, FJ, Krimsky, M, Kaszkin, M and Yedgar, S (2002) "Inhibition of LPS-induced chemokine production in human lung endothelial cells by lipid conjugates anchored to the membrane" *Br J Pharmacol* 135(7):1665-74.

(Continued)

*Primary Examiner* — Sudhakar Katakam
*Assistant Examiner* — Clinton Brooks
(74) *Attorney, Agent, or Firm* — Mark S. Cohen; Pearl Cohen Zedek Latzer, LLP

(57) ABSTRACT

The invention relates to methods of use for compounds in treating, reducing the incidence, reducing the severity or pathogenesis of an intestinal disease or condition in a subject, including, inter alia, inflammatory bowel disease, Crohn's disease, ulcerative colitis, or a combination thereof.

7 Claims, No Drawings

FOREIGN PATENT DOCUMENTS

| WO | WO 98/51285 | 11/1998 |
|---|---|---|
| WO | WO 01/51003 | 7/2001 |
| WO | WO 01/91805 | 12/2001 |
| WO | WO 2005/084307 | 9/2005 |

OTHER PUBLICATIONS

Brenner, T, Arnon, R, Sela, M, Abramsky, O, Meiner, Z, Riven-Kreitman, R, Tarcik, N and Teitelbaum, D (2001) "Humoral and cellular immune responses to Copolymer 1 in multiple sclerosis patients treated with Copaxone" *J Neuroimmunol* 115(1-2):152-60.

Brenner, T, Lisak, RP, Rostami, A, Pleasure, DE and Silberberg, DH (1986) "Astrocytes, oligodendrocytes, and Schwann cells share a common antigenic determinant that cross-reacts with myelin basic protein: identification with monoclonal antibody" *J Neurosci* 6(7):1925-33.

Brenner, T, Poradosu, E, Soffer, D, Sicsic, C, Gazit, A and Levitzki, A (1998) "Suppression of experimental autoimmune encephalomyelitis by tyrphostin AG-556" *Exp Neurol* 154(2):489-98.

Cabanas, C and Hogg, N (1993) "Ligand intercellular adhesion molecule 1 has a necessary role in activation of integrin lymphocyte function-associated molecule 1" *Proc Natl Acad Sci U S A* 90(12):5838-42.

Chen, WM, Soria, J, Soria, C, Krimsky, M and Yedgar, S (2002) "Control of capillary formation by membrane-anchored extracellular inhibitor of phospholipase A(2)" *FEBS Lett* 522(1-3):113-8.

Dan, P, Dagan, A, Krimsky, M, Pruzanski, W, Vadas, P and Yedgar, S (1998) "Inhibition of type I and type II phospholipase A2 by phosphatidyl-ethanolamine linked to polymeric carriers" *Biochemistry* 37(17):6199-204.

Darville, T, Yedgar, S, Krimsky, M, Andrews, CW, Jr., Jungas, T and Ojcius, DM (2004) "Protection against *Chlamydia trachomatis* infection in vitro and modulation of inflammatory response in vivo by membrane-bound glycosaminoglycans" *Microbes Infect* 6(4):369-76.

Davidson, FF, Dennis, EA, Powell, M and Glenney, JR, Jr. (1987) "Inhibition of phospholipase A2 by "lipocortins" and calpactins. An effect of binding to substrate phospholipids" *J Biol Chem* 262(4):1698-705.

Greaves MW and Camp RD (1988) "Prostaglandins, leukotrienes, phospholipase, platelet activating factor, and cytokines: an integrated approach to inflammation of human skin." *Arch Dermatol Res* 280:S33-41.

Krimsky, M, Dagan, A, Aptekar, L, Ligumsky, M and Yedgar, S (2000) "Assessment of intestinal permeability in rats by permeation of inulin-fluorescein" *J Basic Clin Physiol Phamiacol* 11(2):143-53.

Krimsky, M, Yedgar, S, Aptekar, L, Schvvob, O, Goshen, G, Gruzman, A, Sasson, S and Ligumsky, M (2003) "Amelioration of TNBS-induced colon inflammation in rats by phospholipase A2 inhibitor" *Am J Physiol Gastrointest Liver Physiol* 285(3):G586-92.

Margolis-Nunno, H, Ben-Hur, E, Gottlieb, P, Robinson, R, Oetjen, J and Horowitz, B (1996) "Inactivation by phthalocyanine photosensitization of multiple forms of human immunodeficiency virus in red cell concentrates" *Transfusion* 36(8):743-50.

Murthy, SN, Cooper, HS, Shim, H, Shah, RS, Ibrahim, SA and Sedergran, DJ (1993) "Treatment of dextran sulfate sodium-induced murine colitis by intracolonic cyclosporin" *Dig Dis Sci* 38(9):1722-34.

Okayasu, I, Hatakeyama, S; Yamada, M, Ohkusa, T, Inagaki, Y and Nakaya, R (1990) "A novel method in the induction of reliable experimental acute and chronic ulcerative colitis in mice" *Gastroenterology* 98(3):694-702.

Schmiel, DH and Miller, VL (1999) "Bacterial phospholipases and pathogenesis" *Microbes Infect* 1(13):1103-12.

Schnitzer, E, Dagan, A, Krimsky, M, Lichtenberg, D, Pinchuk, I, Shinar, H and Yedgar, S (2000) "Interaction of hyaluronic acid-linked phosphatidylethanolamine (HyPE) with LDL and its effect on the susceptibility of LDL lipids to oxidation" *Chem Phys Lipids* 104(2):149-60.

Schnitzer, E, Yedgar, S, Danino, D, Talmon, Y and Lichtenberg, D (1999) "The Interaction of hyaluronic-phosphatidylethanolamine with low density lipoprotein (LDL) and its effect on copper induced LDL oxidation" *Biophysical Journal* 76(1): Part 2.

Schnitzer, E, Pinchuk, I, Fainaru, M, Lichtenberg, D and Yedgar, S (1998) "LDL-associated phospholipase A does not protect LDL against lipid peroxidation in vitro" *Free Radic Biol Med* 24(7-8):1294-303.

Yard, BA, Yedgar, S, Scheele, M, Van Der Woude, D, Beck, G, Heidrich, B, Krimsky, M, Van Der Woude, FJ and Post, S (2002) "Modulation of IFN-gamma-induced immunogenicity by phosphatidylethanolamine-linked hyaluronic acid" *Transplantation* 73(6):984-92.

Yedgar, S, Lichtenberg, D and Schnitzer, E (2000) "Inhibition of phospholipase A(2) as a therapeutic target" *Biochim Biophys Acta* 1488(1-2):182-7.

Wang D.P, Matthias Schuster, Yi Fong Wang, Chi Huey Wong "Synthesis of phospholipid-inhibitor conjugates by enzymic transphosphatidylation with phospholipase", J. Am. Chem. Soc.; 1993; 115(23); 10487-10491.

Carey et al, "Contrasting effects of cycloxygenase-1 (cox-1) and cox-2 deficiency in the host response to influenze, a viral infection". Journ. Of Immunology 2005, vol. 15: 175 (10): 6878-84.

Teitelbaum D, Arnon R, Sela M, Rabinsohn Y, Shapiro D., "Sphingomyelin specific antibodies elicited by synthetic conjugates," Immunochemistry. Nov. 1973;10(11):735-43.

Weltzien HU, Matthiessen HP, Meyer-Delius M, Zimmermann F, Rüde E., "Acidic "peptidophospholipids", a new class of hapten-bearing cell surface modifying reagents," Mol Immunol. Sep. 1984;21(9):801-10.

Winger TM, Ludovice PJ, Chaikof EL, "Lipopeptide conjugates: biomolecular building blocks for receptor activating membrane-mimetic structures," Biomaterials. Feb. 1996;17(4):437-41.

Office Action of U.S. Appl. No. 11/220,965 dated Mar. 27, 2008.

Office Action of U.S. Appl. No. 10/989,606 dated Sep. 1, 2009.

Supplementary Search Report of European Application No. 05724186.1 dated Nov. 17, 2009.

Office Action of Japanese Application No. 2001-551427 dated Nov. 20, 2009.

Extended European Search Report of European Application No. 05808267.8 issued Mar. 15, 2012.

Phyllis, Dan et al., "Inhibition of Type I and Type II Phospholipase A2 by Phosphatidyl-Ethanolamine Linked to Polymeric Carriers," Biochemistry, 1998, 37 (17), pp. 6199-6204.

\* cited by examiner

USE OF LIPID CONJUGATES IN THE TREATMENT OF DISEASE

CROSS REFERENCE TO RELATED APPLICATIONS

This application is a continuation-in-part application of U.S. patent application Ser. No. 10/790,182, filed Mar. 2, 2004 now U.S. Pat. No. 7,141,552 and U.S. patent application Ser. No. 10/952,496, filed Sep. 29, 2004, now U.S. Pat. No. 7,393,938 which are continuation-in-part applications of U.S. patent application Ser. No. 09/756,765, filed Jan. 10, 2001, now U.S. Pat. No. 7,034,006 which claims priority from U.S. Provisional Patent Application Ser. No. 60/174,907, filed Jan. 10, 2000, which are hereby incorporated by reference.

FIELD OF THE INVENTION

This invention provides methods of use for compounds in treating, reducing the incidence, reducing the severity or pathogenesis of an intestinal disease or condition in a subject, including, inter alia, inflammatory bowel disease, Crohn's disease, ulcerative colitis, or a combination thereof.

BACKGROUND OF THE INVENTION

Lipid-conjugates are thought to inhibit the enzyme phospholipase A2 (PLA2, EC 3.1.1.4). Phospholipase A2 catalyzes the breakdown of phospholipids at the sn-2 position to produce a fatty acid and a lysophospholipid. The activity of this enzyme has been correlated with various cell functions, particularly with the production of lipid mediators such as eicosanoid production (prostaglandins, thromboxanes and leukotrienes), platelet activating factor and lysophospholipids. Lipid-conjugates may offer a wider scope of protection of cells and organisms from injurious agents and pathogenic processes, including the prevention and treatment of dermatologic conditions.

SUMMARY OF THE INVENTION

This invention provides methods of use for compounds represented by the structure of the general formula (A):

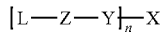
(A)

wherein L is phosphatidylethanolamine; Z is either nothing, ethanolamine, serine, inositol, choline, or glycerol; Y is either nothing or a spacer group ranging in length from 2 to 30 atoms; X is hyaluronic acid; and n is a number from 1 to 1000; and/or a pharmaceutically acceptable salt or a pharmaceutical product thereof, wherein said compound is administered at a dose of 5 mg/ml for reducing the incidence, reducing the severity or pathogenesis of an intestinal disease or condition in a subject, including, inter alia, inflammatory bowel disease, Crohn's disease, ulcerative colitis, or a combination thereof.

This invention also provides methods of use for compounds represented by the structure of the general formula (A):

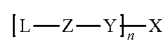
(A)

wherein L is a lipid or a phospholipid; Z is either nothing, ethanolamine, serine, inositol, choline, or glycerol; Y is either nothing or a spacer group ranging in length from 2 to 30 atoms; X is a physiologically acceptable monomer, dimer, oligomer, or polymer; and n is a number from 1 to 1000; and/or a pharmaceutically acceptable salt or a pharmaceutical product thereof, for reducing the incidence, reducing the severity or pathogenesis of an intestinal disease or condition in a subject, including, inter alia, inflammatory bowel disease, Crohn's disease, ulcerative colitis, or a combination thereof.

DETAILED DESCRIPTION OF THE PRESENT INVENTION

In one embodiment, this invention provides a method of treating an intestinal disease or condition in a subject, comprising the step of administering to said subject a compound represented by the structure of the general formula (A):

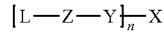
(A)

wherein L is phosphatidylethanolamine; Z is either nothing, ethanolamine, serine, inositol, choline, or glycerol; Y is either nothing or a spacer group ranging in length from 2 to 30 atoms; X is hyaluronic acid; and n is a number from 1 to 1000; and/or a pharmaceutically acceptable salt or a pharmaceutical product thereof, wherein said compound is administered at a dose of 5 mg/ml.

In another embodiment, this invention provides a method of reducing the incidence, reducing the severity or pathogenesis of an intestinal disease or condition in a subject, comprising the step of administering to said subject a compound represented by the structure of the general formula (A):

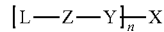
(A)

wherein L is a lipid or a phospholipid; Z is either nothing, ethanolamine, serine, inositol, choline, or glycerol; Y is either nothing or a spacer group ranging in length from 2 to 30 atoms; X is a physiologically acceptable monomer, dimer, oligomer, or polymer; and n is a number from 1 to 1000; and/or a pharmaceutically acceptable salt or a pharmaceutical product thereof.

In one embodiment, an intestinal disease or disorder comprises Appendicitis, Cancer, Celiac Disease, Crohn's Disease, Constipation, Diarrhea, Diverticulitis, GERD (Gastro Esophageal Reflux Disease), Hemorrhoids, Hernias, Hiatus Hemia, Inflammatory Bowel Disease, Intestinal Gas, Irritable Bowel Syndrome, Lactose Intolerance, Necrotizing Enterocolitis, Non-Ulcer Dyspepsia, Ostomies, Pancreatitis, Pseudomembranous Colitis, Short Bowel Syndrome, Ulcerative Colitis, Ulcer Disease, Ulcerative Proctitis, traveler's diarrhea, drug-related diarrhea polyps, absorption disorders, vascular disease of the intestines, intestinal obstruction, intestinal infections, Shigellosis, cholera, amebiasis, enteric fever, Whipple's Disease, peritonitis, intraabdominal abcesses, hereditary hemochromatosis, gastroenteritis, viral gastroenteritis, food poisoning, mesenteric ischemia, mesenteric infarction, metabolic diseases and/or disorders, or a combination thereof. In another embodiment, compounds for use in the present invention may be used to treat Acute Abdominal Pain; Acute Mesenteric Ischemia; Acute Perforation; Appendicitis, Hernias of the Abdominal Wall; Ileus; Intestinal obstruction; Intra-abdominal abcesses; Ischemic Colitis; Anorectal conditions comprising Anal Fissure; Anorectal Abscess; Anorectal Fistula; Fecal Incontinence; Hemorrhoids; Levator Syndrome; Pilonidal Disease, Proctitis; Pruritus Ani; Rectal Prolapse and Procidentia; Lower GI Complaints comprising Constipation; Fecal impaction; Dyschezia; Diarrhea; Gas-Related Complaints comprising Excessive belching; Distention (bloating); Excessive flatus; Irritable Bowel Syndrome (IBS); Upper GI Complaints comprising Chest Pain; Chronic and Recurrent Abdominal Pain; Dyspepsia; Functional GI Illness; Globus Sensation; Hiccups; Nausea and Vomiting; Rumination; Bezoars; Foreign Bodies comprising Esophageal foreign bodies; Gastric and intestinal foreign bodies; Rectal foreign bodies; Diverticular Disease comprising Diverticular Disease of the Stomach and Small Bowel; Diverticulitis; Diverticulosis; Meckel's Diverticulum; Esophageal and Swallowing Disorders; Dysphagia; Oropharyngeal Dysphagia; Esophageal Dysphagia; Cricopharyngeal Incoordination; Esophageal Diverticula; Esophageal Rupture; Gastroesophageal Reflux Disease (GERD); Hiatus Hernia; Infectious Esophageal Disorders; Mallory-Weiss Syndrome; Motility Disorders; Achalasia; Symptomatic Diffuse Esophageal Spasm; Obstructive Disorders; Gastritis and Peptic Ulcer Disease; Autoimmune Metaplastic Atrophic Gastritis; Nonerosive Gastritis; Superficial gastritis; Deep gastritis; Gastric atrophy; Metaplasia; Postgastrectomy Gastritis; Uncommon Gastritis Syndromes; Menetrier's disease; Eosinophilic gastritis; Mucosa-associated lymphoid tissue (MALT) lymphoma (pseudolymphoma); Infectious (septic) gastritis; Helicobacter pylori Infection; Peptic Ulcer Disease; Hemorrhage; Penetration (confined perforation); Free perforation; Gastric outlet obstruction; Stomach cancer; Gastroenteritis; Drug-Related Gastroenteritis; Traveler's Diarrhea; GI Bleeding comprising Varices; Vascular GI Lesions; Malabsorption Syndromes; Bacterial Overgrowth Syndrome; Carbohydrate Intolerance; Celiac Sprue; Infection and Infestation; Intestinal Lymphangiectasia; Short Bowel Syndrome; Tropical Sprue; Whipple's Disease; Pancreatitis; Acute Pancreatitis; Chronic Pancreatitis; Tumors of the GI Tract; Benign Esophageal Tumors; Colorectal Cancer; Esophageal Cancer; Gastrointestinal Stromal Tumors; Pancreatic Cancer; Pancreatic Endocrine Tumors; Insulinoma; Polyps of the Colon and Rectum; Small-Bowel Tumors; Stomach Cancer; or a combination thereof. In one embodiment, an intestinal disease or disorder comprises immuno-inflammatory intestinal injury, drug-induced enteropathy, and/or ischemia-induced intestinal injury.

Colitis is a chronic disease of the gastrointestinal lumen, marked by abdominal discomfort, diarrhea and, upon radiological or histological diagnosis, characteristic signs of mucosal damage including epithelial denudation. Crohn's disease is a related disorder affecting typically the small intestine but which may involve any region of the gastrointestinal tract.

Inflammatory bowel disease (IBD) is a common and chronic gastrointestinal disorder characterized by intestinal inflammation and mucosal tissue damage initiated and perpetuated by a dysregulated immune response along with several intra- and extraintestinal manifestations, including autoimmune phenomena. The administration of DSS dissolved in water to mice causes hematochezia, body weight loss, shortening of the intestine, mucosal ulcers, and infiltration of neutrophils, as is shown in the Examples section hereinbelow. This procedure is a well-accepted model for IBD.

In one embodiment, "treating" refers to both therapeutic treatment and prophylactic or preventative measures, wherein the object is to prevent or lessen the targeted pathologic condition or disorder as described hereinabove. Thus, in one embodiment, treating may include suppressing, inhibiting, preventing, treating, or a combination thereof. Thus, in one embodiment, "treating" refers inter alia to increasing time to sustained progression, expediting remission, inducing remission, augmenting remission, speeding recovery, increasing efficacy of or decreasing resistance to alternative therapeutics, or a combination thereof. In one embodiment, "preventing" refers inter alia to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of an intestinal disease, while in one embodiment, "secondary" refers to a symptom that is derived from or consequent to a primary cause. In one embodiment, the compounds for use in the present invention treat primary or secondary symptoms or secondary complications related to an intestinal disease. In another embodiment, the compounds for use in the present invention treat primary or secondary symptoms or secondary complications related to an intestinal disease or disorder.

In another embodiment, "symptoms" may be any manifestation of a disease or pathological condition, comprising inflammation, swelling, fever, pain, bleeding, itching, runny nose, coughing, headache, migraine, dizziness, blurry vision, diarrhea, vomiting, constipation, gas, indigestion, etc.

Thus, in one embodiment of the present invention, the compounds for use in the present invention are directed towards the resolution of symptoms of a disease or disorder of the intestines. In another embodiment, the compounds affect the pathogenesis underlying a disease or disorder of the intestines.

In one embodiment, a disease or disorder of the intestines may affect a cell, in one embodiment, a vertebrate cell, in another embodiment, a mammalian cell, and in another embodiment, a human cell. It is to be understood that compounds of the present invention may be efficacious in treating any cell type in which a disease or disorder of the intestines is present or in which the causes of a disease or disorder of the intestines may exert an effect. In one embodiment, a compound for use in the present invention may localize to or act on a specific cell type. In one embodiment, a compound for use in the present invention may be cytoprotective. In one embodiment a compound for use in the present invention may be inserted or partially inserted into a cell membrane. In another embodiment a compound for use in the present invention may be effective in treating a plurality of cell types.

In one embodiment, a disease or disorder of the intestines is a primary or secondary symptom of an underlying illness, which in one embodiment, is an autoimmune disease.

In one embodiment, the methods of the present invention may be used to treat a disease or disorder of the intestines in a subject that is immunosuppressed, while in another embodiment, in a subject that is immunodeficient, while in another embodiment, in a subject that is immunocompetent.

Administration of the compounds for use in the present invention invoke remarkable, and unexpected, cytoprotective effects, which are useful in the prevention and treatment of intestinal diseases and/or conditions.

In one embodiment of the present invention, the useful pharmacological properties of the compounds for use in the present invention, some of which are described hereinabove, may be applied for clinical use, and disclosed herein as methods for the prevention or treatment of a disease. The biological basis of these methods may be readily demonstrated by standard cellular and animal models of disease.

In one embodiment, the pharmacological activities of compounds for use in the present invention, including membrane stabilization, anti-inflammation, anti-oxidant action, and attenuation of chemokine levels, may contribute to a treated cell's resistance to diseases of the intestines. In one embodiment, cell membrane stabilization may ameliorate or prevent tissue injury arising in the course of an intestinal disease. In another embodiment, anti-oxidant action may limit oxidative damage to cell and blood components arising in the course of an intestinal disease. In another embodiment, attenuation of chemokine levels may attenuate physiological reactions to stress that arise in the course of an intestinal disease.

In one embodiment of the invention, the compounds for use in the present invention described herein can be used to treat disease, through amelioration, or prevention, of tissue injury arising in the course of pathological disease states by stabilizing cell membranes; limiting oxidative damage to cell and blood components; or attenuating physiological reactions to stress, as expressed in elevated chemokine levels.

In one embodiment, methods of the present invention involve treating a subject by inter alia controlling the expression, production, and activity of phospholipases such as PLA2; controlling the production and/or action of lipid mediators, such as eicosanoids, platelet activating factor (PAF) and lyso-phospholipids; amelioration of damage to cell surface glycosaminoglycans (GAG) and proteoglycans; controlling the production of oxidants, oxygen radicals and nitric oxide; protection of cells, tissues, and plasma lipoproteins from damaging agents, such as reactive oxygen species (ROS) and phospholipases; controlling the expression, production, and activity of cytokines, chemokines and interleukins; anti-oxidant therapy; anti-endotoxin therapy or any combination thereof.

In one embodiment of the invention, the term "controlling" refers to inhibiting the production and action of the above mentioned factors in order to maintain their activity at the normal basal level and suppress their activation in pathological conditions.

In one embodiment of the invention, intestinal disease is characterized by the presence of damaging agents, which comprise, inter alia, phospholipases, reactive oxygen species (ROS), free radicals, lysophospholipids, fatty acids or derivatives thereof, hydrogen peroxides, phospholipids, oxidants, cationic proteins, streptolysins, proteases, hemolysins, or sialidases.

Dosages and Routes of Administration

This invention encompasses administration of compounds as described herein or compositions comprising the same, for treating intestinal diseases.

In one embodiment, compositions of this invention are pharmaceutically acceptable. In one embodiment, the term "pharmaceutically acceptable" refers to any formulation which is safe, and provides the appropriate delivery for the desired route of administration of an effective amount of at least one compound for use in the present invention. This term refers to the use of buffered formulations as well, wherein the pH is maintained at a particular desired value, ranging from pH 4.0 to pH 9.0, in accordance with the stability of the compounds and route of administration.

In some embodiments, any of the compositions of this invention will comprise a compound of the present invention, in any form or embodiment as described herein. In some embodiments, any of the compositions of this invention will consist of a compound of the present invention, in any form or embodiment as described herein. In some embodiments, the compositions of this invention will consist essentially of a compound of the present invention, in any form or embodiment as described herein. In some embodiments, the term "comprise" refers to the inclusion of the indicated active agent, such as the Compounds I-C, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In one embodiment, a Compound used in the methods of this invention may be administered alone or within a composition. In another embodiment, compositions comprising compounds for use in the present invention in admixture with conventional excipients, i.e. pharmaceutically acceptable organic or inorganic carrier substances suitable for parenteral, enteral (e.g., oral) or topical application which do not deleteriously react with the active compounds may be used. In one embodiment, suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. In another embodiment, the pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In another embodiment, they can also be combined where desired with other active agents, e.g., vitamins.

In one embodiment, the therapeutic compositions of the instant invention comprise a compound of the instant invention and additional compounds effective in preventing or treating intestinal disease. In one embodiment, the additional compounds comprise anti-inflammatory compositions, which in one embodiment are non-steroidal anti-inflammatory medications, antihistamines, antibiotics, corticosteroids, cromolyn sodium (sodium cromoglicate), mast-cell stabilizers, or a combination thereof. In one embodiment, antibiotics comprise chloramphenicol, fusidic acid, tetracycline, erythromycin, gentamycin, or a combination thereof. In another embodiment, an additional compound is vitamin A.

In one embodiment, the therapeutic compositions of the instant invention are administered with other treatments that relieve symptoms.

In one embodiment, the route of administration may be parenteral, enteral, or a combination thereof. In another embodiment, the route may be intra-ocular, topical, transdermal, intradermal, subcutaneous, intraperitoneal, intravenous, intra-arterial, vaginal, rectal, intratumoral, parcanceral, transmucosal, intramuscular, intravascular, intraventricular, intracranial, inhalation, nasal aspiration (spray), sublingual, oral, aerosol or suppository or a combination thereof. In one embodiment, the dosage regimen will be determined by skilled clinicians, based on factors such as exact nature of the condition being treated, the severity of the condition, the age and general physical condition of the patient, etc.

For parenteral application, particularly suitable are injectable, sterile solutions, preferably oily or aqueous solutions, as well as suspensions, emulsions, or implants, including suppositories and enemas. Ampoules are convenient unit dosages. Such a suppository may comprise any agent described herein.

For application by inhalation, solutions or suspensions of the compounds mixed and aerosolized or nebulized in the presence of the appropriate carrier suitable. Such an aerosol may comprise any agent described herein and, in one embodiment, may be used to treat diseases or conditions caused by airborne pathogens, which may in one embodiment, cause intestinal disorders.

For topical application, an admixture of the compounds with conventional creams, lotions, or delayed release patches is acceptable. Such a cream or lotion may comprise any agent described herein, and, in one embodiment, may be used to treat an intestinal disease.

For enteral application, particularly suitable are tablets, dragees, liquids, drops, or capsules. A syrup, elixir, or the like can be used when a sweetened vehicle is employed.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilisates obtained, for example, for the preparation of products for injection.

Thus, in one embodiment, the route of administration may be directed to an organ or system that is affected by an intestinal disease. For example, compounds may be administered in intra-peritoneal form to treat an intestinal disease. In another embodiment, the route of administration may be directed to a different organ or system than the one that is affected by an intestinal disease. For example, compounds may be administered intravenously to treat an intestinal disease. Thus, the present invention provides for the use of compounds of the instant invention in various dosage forms suitable for administration using any of the routes listed hereinabove.

In general, the doses utilized for the above described purposes will vary, but will be in an effective amount to exert the desired effect. As used herein, the term "pharmaceutically effective amount" refers to an amount of a compound of formulae A and I-C as described hereinabove, which will produce the desired alleviation in symptoms or other desired phenotype in a patient. The doses utilized for any of the above-described purposes will generally be from 1 to about 1000 milligrams per kilogram of body weight (mg/kg), administered one to four times per day, or by continuous IV infusion. In one embodiment, compounds may be administered at a concentration of 5 mg/ml, while in another embodiment, compounds may be administered at a concentration of 20 mg/ml. In another embodiment, compounds may be administered at 1, 2, 3, 4, 7, 10, 12, 15, 17, or 25 mg/ml. In one embodiment, compounds may be administered by gavage, while in another embodiment, they may be administered orally. In one embodiment, compounds are administered three times per day, while in another embodiment, compounds are administered continuously, such as via drinking water or intravenous feed. In another embodiment, compounds are administered once per day, and in another embodiment, two times per day, four times per day or five times per day.

When the compositions are dosed topically or intraocularly, they will generally be in a concentration range of from 0.1 to about 10% w/v, administered 14 times per day.

In one embodiment of the invention, the concentrations of the compounds will depend on various factors, including the nature of the condition to be treated, the condition of the patient, the route of administration and the individual tolerability of the compositions.

It will be appreciated that the actual preferred amounts of active compound in a specific case will vary according to the specific compound being utilized, the particular compositions formulated, the mode of application, and the particular conditions and organism being treated. Dosages for a given host can be determined using conventional considerations, e.g., by customary comparison of the differential activities of the subject compounds and of a known agent, e.g., by means of an appropriate, conventional pharmacological protocol.

In one embodiment, the compounds of the invention may be administered acutely for acute treatment of temporary conditions, or may be administered chronically, especially in the case of progressive, recurrent, or degenerative disease. In one embodiment, one or more compounds of the invention may be administered simultaneously, or in another embodiment, they may be administered in a staggered fashion. In one embodiment, the staggered fashion may be dictated by the stage or phase of the disease.

In one embodiment, the present invention offers methods for the treatment of disease based upon administration of lipids covalently conjugated through their polar head group to a physiologically acceptable chemical moiety, which may be of high or low molecular weight.

The present invention has been illustrated in terms of the anti-disease activity of compounds for use in the present invention and methods of their use as pharmaceutical compositions in the treatment of disease. The following sections present some examples of the therapeutic compounds for use in the present invention and their chemical preparation.

Compounds

In one embodiment, the compounds for use in the present invention comprise a lipid or phospholipid moiety bound to a physiologically acceptable monomer, dimer, oligomer, or polymer. In one embodiment, the physiologically acceptable monomer, dimer, oligomer, or polymer is salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate, a dipeptide, a disaccharide, a trisaccharide, an oligosaccharide, a polysaccharide, a hetero-polysaccharide, a homo-polysaccharide, a polypyranose, an oligopeptide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid, a glycosaminoglycan, polygeline ('haemaccel'), alginate, hydroxyethyl starch (hetastarch), polyethylene glycol, polycarboxylated polyethylene glycol, chondroitin-6-sulfate, chondroitin-4-sulfate, keratin, keratin sulfate, heparan sulfate, dermatin, dermatan sulfate, carboxymethylcellulose, heparin, dextran, or hyaluronic acid.

In one embodiment, examples of polymers which can be employed as the conjugated moiety for producing compounds for use in the methods of this invention may be physiologically acceptable polymers, including water-dispersible or -soluble polymers of various molecular weights and diverse chemical types, mainly natural and synthetic polymers, such as glycosaminoglycans, hyaluronic acids, heparin, heparin sulfates, chondroitin sulfates, chondroitin-6-sulfates, chondroitin-4-sulfates, keratins, keratin sulfates, dermatins, dermatan sulfates, dextrans, plasma expanders, including polygeline ("Haemaccel", degraded gelatin polypeptide cross-linked via urea bridges, produced by "Behring"), "hydroxyethylstarch" (Hetastarch, HES) and extrans, food and drug additives, soluble cellulose derivatives (e.g., methylcellulose, carboxymethylcellulose), polyaminoacids, hydrocarbon polymers (e.g., polyethylene), polystyrenes, polyesters, polyamides, polyethylene oxides (e.g. polyethyleneglycols, polycarboxyethyleneglycols, polycarboxylated polyethyleneglycols), polyvinnylpyrrolidones, polysaccharides, polypyranoses, alginates, assimilable gums (e.g., xanthan gum), peptides, injectable blood proteins (e.g., serum albumin), cyclodextrin, and derivatives thereof.

In one embodiment, examples of monomers, dimers, and oligomers which can be employed as the conjugated moiety for producing compounds for use in the present invention for use in the methods of the invention may be mono- or di-saccharides, trisaccharides, oligopeptides, carboxylic acids, dicarboxylic acids, fatty acids, dicarboxylic fatty acids, salicylates, salicyclic acids, acetyl salicylic acids, aspirins, lactobionic acids, maltoses, amino acids, glycines, glutaric acids, succinic acids, dodecanoic acids, didodecanoic acids, bile acids, cholic acids, cholesterylhemisuccinates, and di- and trisaccharide unit monomers of polysaccharides, polypyranoses, and/or glycosaminoglycans including heparins, heparan sulfates, hyaluronic acids, chondroitins, chondroitin sulfates, chondroitin-6-sulfates, chondroitin-sulfates, dermatins, dermatan sulfates, keratins, keratan sulfates, or dextrans.

In one embodiment, the lipid compounds for use in the present invention are described by the general formula:

[phosphatidylethanolamine-Y]n-X

[phosphatidylserine-Y]n-X

[phosphatidylcholine-Y]n-X

[phosphatidylinositol-Y]n-X

[phosphatidylglycerol-Y]n-X

[phosphatidic acid-Y]n-X

[lyso-phospholipid-Y]n-X

[diacyl-glycerol-Y]n-X

[monoacyl-glycerol-Y]n-X

[sphingomyelin-Y]n-X

[sphingosine-Y]n-X

[ceramide-Y]n-X wherein

Y is either nothing or a spacer group ranging in length from 2 to 30 atoms; and

X is a physiologically acceptable monomer, dimer, oligomer or polymer; and n is the number of lipid molecules bound to a molecule of X, wherein n is a number from 1 to 1000.

In one embodiment, the invention provides low-molecular weight compounds, previously undisclosed and unknown to possess pharmacological activity, of the general formula described hereinabove. In another embodiment, wherein the general formula described hereinabove describes low-molecular weight compounds, X is a mono- or di-saccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisacharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid.

In one embodiment of this invention, X is any of the physiologically acceptable monomer, dimer, oligomer, or polymer, as described herein. In one embodiment, X is conjugated to the lipid, phospholipid, or spacer via an ester bond. In another embodiment, X is conjugated to the lipid, phospholipid, or spacer via an amide bond.

As defined by the structural formulae provided herein for the compounds for use in the present invention, these compounds may contain between one to one thousand lipid moieties bound to a single physiologically acceptable polymer molecule. In one embodiment of this invention, n is a number from 1 to 1000. In another embodiment, n is a number from 1 to 500. In another embodiment, n is a number from 1 to 100. In another embodiment, n is a number from 2 to 1000. In another embodiment, n is a number from 2 to 100. In another embodiment, n is a number from 2 to 200. In another embodiment, n is a number from 3 to 300. In another embodiment, n is a number from 10 to 400. In another embodiment, n is a number from 50 to 500. In another embodiment, n is a number from 100 to 300. In another embodiment, n is a number from 300 to 500. In another embodiment, n is a number from 500 to 800. In another embodiment, n is a number from 500 to 1000.

In one embodiment of the invention, when the conjugated moiety is a polymer, the ratio of lipid moieties covalently bound may range from one to one thousand lipid residues per polymer molecule, depending upon the nature of the polymer and the reaction conditions employed. For example, the relative quantities of the starting materials, or the extent of the reaction time, may be modified in order to obtain products with either high or low ratios of lipid residues per polymer, as desired.

In one embodiment, the set of compounds comprising phosphatidylethanolamine covalently bound to a physiologically acceptable monomer, dimmer, oligomer, or polymer, is referred to herein as the PE-conjugates. In one embodiment, the phosphatidylethanolamine moiety is dipalmitoyl phosphatidylethanolamine. In another embodiment, the phosphatidylethanolamine moiety is dimyristoyl phosphatidylethanolamine. In another embodiment, related derivatives, in which either phosphatidylserine, phosphatidylcholine, phosphatidylinositol, phosphatidic acid or phosphatidylglycerol are employed in lieu of phosphatidylethanolamine as the lipid moiety provide equivalent therapeutic results, based upon the structural similarities shared by these compounds.

In another embodiment, the lipid or phospholipid moiety is phosphatidic acid, an acyl glycerol, monoacylglycerol, diacylglycerol, triacylglycerol, sphingosine, sphingomyelin, chondroitin-4-sulfate, chondroitin-6-sulfate, ceramide, phosphatidylethanolamine, phosphatidylserine, phosphatidylcholine, phosphatidylinositol, or phosphatidylglycerol, or an ether or alkyl phospholipid derivative thereof.

In one embodiment, derivatives relevant to this invention are compounds wherein at least one of the fatty acid groups of the lipid moieties at position C1 or C2 of the glycerol backbone are substituted by a long chain alkyl group attached by amide, ether or alkyl bonds, rather than ester linkages.

In the methods, according to embodiments of the invention, the compounds for use in the present invention administered to the subject are comprised from at least one lipid moiety covalently bound through an atom of the polar head group to a monomeric or polymeric moiety (referred to herein as the conjugated moiety) of either low or high molecular weight. When desired, an optional bridging moiety can be used to link the compounds for use in the present invention moiety to the monomer or polymeric moiety. The conjugated moiety may be a low molecular weight carboxylic acid, dicarboxylic acid, fatty acid, dicarboxylic fatty acid, acetyl salicylic acid, cholic acid, cholesterylhemisuccinate, or mono- or di-saccharide, an amino acid or dipeptide, an oligopeptide, a glycoprotein mixture, a di- or trisaccharide monomer unit of a glycosaminoglycan such as a repeating unit of heparin, heparan sulfate, hyaluronic acid, chondroitin-sulfate, denmatan, keratan sulfate, or a higher molecular weight peptide or oligopeptide, a polysaccharide, a hetero-polysaccharide, a homo-polysaccharide, a polypyranose, polyglycan, protein, glycosaminoglycan, or a glycoprotein mixture. The composition of some phospholipid-conjugates of high molecular weight, and associated analogues, are the subject of U.S. Pat. No. 5,064,817, which is incorporated herein in its entirety by reference.

In one embodiment, the term "moiety" means a chemical entity otherwise corresponding to a chemical compound, which has a valence satisfied by a covalent bond.

In some cases, according to embodiments of the invention, the monomer or polymer chosen for preparation of the compound may in itself have select biological properties. For example, both heparin and hyaluronic acid are materials with known physiological functions. In the present invention, however, the compounds for use in the present invention formed from these substances as starting materials display a new and wider set of pharmaceutical activities than would be predicted from administration of either heparin or hyaluronic acid which have not been bound by covalent linkage to a phospholipid. In some embodiments, phosphatidylethanolamine (PE) linked to hyaluronic acid (Compound XXII), to heparin (Compound XXIV), to chondroitin sulfate A (Compound XXV), to carboxymethylcellulose (Compound XXVI), to Polygeline (haemaccel) (Compound XXVII), to alginate (Compound LI), or to hydroxyethylstarch (Compound XXVIII), are useful for methods and in compositions as herein described but perform unexpectedly in terms of potency and range of useful pharmaceutical activity compared to the free conjugates. Thus, the combination of a phospholipid such as phosphatidylethanolamine, or related phospholipids which differ with regard to the polar head group, such as phosphatidylserine (PS), phosphatidylcholine (PC), phosphatidylinositol (PI), and phosphatidylglycerol (PG), results in the formation of a compound which has novel pharmacological properties when compared to the starting materials alone. In one embodiment, such properties may include: greater local persistence, greater anti-inflammatory properties, greater antioxidant activity, or a combination thereof.

The biologically active compounds for use in the present invention described herein can have a wide range of molecular weights, e.g., above 50,000 (up to a few hundred thousands) when it is desirable to retain the Lipid conjugate in the vascular system and below 50,000 when targeting to extravascular systems is desirable. The sole limitation on the molecular weight and the chemical structure of the conjugated moiety is that it does not result in a compound devoid of the desired biological activity, or lead to chemical or physiological instability to the extent that the Compound is rendered useless as a drug in the method of use described herein.

In one embodiment, the compound for use in the present invention is represented by the structure of the general formula (A):

(A)

wherein
L is a lipid or a phospholipid;
Z is either nothing, ethanolamine, serine, inositol, choline, phosphate, or glycerol;
Y is either nothing or a spacer group ranging in length from 2 to 30 atoms;
X is a physiologically acceptable monomer, dimer, oligomer, or polymer; and
n is a number from 1 to 1000;
wherein any bond between L, Z, Y and X is either an amide or an esteric bond.

In one embodiment, L is phosphatidyl, Z is ethanolamine, wherein L and Z are chemically bonded resulting in phosphatidylethanolamine, Y is nothing, and X is carboxymethylcellulose. In another embodiment, L is phosphatidyl, Z is ethanolamine, wherein L and Z are chemically bonded resulting in phosphatidylethanolamine, Y is nothing, and X is a glycosaminoglycan. In one embodiment, the phosphatidylethanolamine moiety is dipalmitoyl phosphatidylethanolamine. In another embodiment, the phosphatidylethanolamine moiety is dimyristoyl phosphatidylethanolamine.

In another embodiment, the compound for use in the present invention is represented by the structure of the general formula (I):

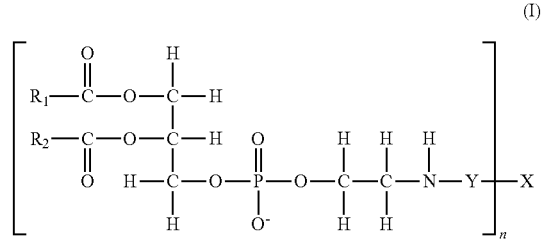

(I)

wherein
$R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms; and

X is either a physiologically acceptable monomer, dimer, oligomer or a physiologically acceptable polymer; and n is a number from 1 to 1,000;

wherein if Y is nothing the phosphatidylethanolamine is directly linked to X via an amide bond and if Y is a spacer, the spacer is directly linked to X via an amide or an esteric bond and to the phosphatidylethanolamine via an amide bond.

In one embodiment, compounds for use in the methods of the invention comprise one of the following as the conjugated moiety X: acetate, butyrate, glutarate, succinate, dodecanoate, didodecanoate, maltose, lactobionic acid, dextran, alginate, aspirin, cholate, cholesterylhemisuccinate, carboxymethyl-cellulose, heparin, hyaluronic acid, chondroitin sulfate, polygeline (haemaccel), hydroxyethylstarch (Hetastarch, HES) polyethyleneglycol, polycarboxylated polyethylene glycol, a glycosaminoglycan, a polysaccharide, a hetero-polysaccharide, a homo-polysaccharide, or a polypyranose. The polymers used as starting material to prepare the PE-conjugates may vary in molecular weight from 1 to 2,000 kDa.

Examples of phosphatidylethanolamine (PE) moieties are analogues of the phospholipid in which the chain length of the two fatty acid groups attached to the glycerol backbone of the phospholipid varies from 2-30 carbon atoms length, and in which these fatty acids chains contain saturated and/or unsaturated carbon atoms. In lieu of fatty acid chains, alkyl chains attached directly or via an ether linkage to the glycerol backbone of the phospholipid are included as analogues of PE. In one embodiment, the PE moiety is dipalmitoyl-phosphatidyl-ethanolamine. In another embodiment, the PE moiety is dimyristoyl-phosphatidyl-ethanolamine.

Phosphatidyl-ethanolamine and its analogues may be from various sources, including natural, synthetic, and semisynthetic derivatives and their isomers.

Phospholipids which can be employed in lieu of the PE moiety are N-methyl-PE derivatives and their analogues, linked through the amino group of the N-methyl-PE by a covalent bond; N,N-dimethyl-PE derivatives and their analogues linked through the amino group of the N,N-dimethyl-PE by a covalent bond, phosphatidylserine (PS) and its analogues, such as palmitoyl-stearoyl-PS, natural PS from various sources, semisynthetic PSs, synthetic, natural and artifactual PSs and their isomers. Other phospholipids useful as conjugated moieties in this invention are phosphatidylcholine (PC), phosphatidylinositol (PI), phosphatidic acid and phosphoatidylglycerol (PG), as well as derivatives thereof comprising either phospholipids, lysophospholipids, phosphatidic acid, sphingomyelins, lysosphingomyelins, ceramide, and sphingosine.

For PE-conjugates and PS-conjugates, the phospholipid is linked to the conjugated monomer or polymer moiety through the nitrogen atom of the phospholipid polar head group, either directly or via a spacer group. For PC, PI, and PG conjugates, the phospholipid is linked to the conjugated monomer or polymer moiety through either the nitrogen or one of the oxygen atoms of the polar head group, either directly or via a spacer group.

In another embodiment, the compound for use in the present invention is represented by the structure of the general formula (II):

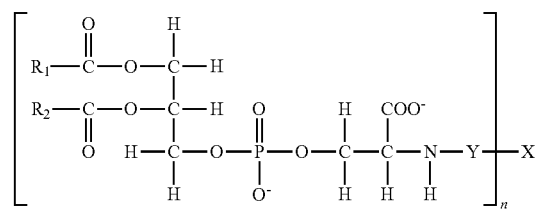

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a glycosaminoglycan; and n is a number from 1 to 1000;

wherein if Y is nothing, the phosphatidylserine is directly linked to X via an amide bond and if Y is a spacer, the spacer is directly linked to X via an amide or an esteric bond and to the phosphatidylserine via an amide bond.

In one embodiment, the phosphatidylserine may be bonded to Y, or to X if Y is nothing, via the $COO^-$ moiety of the phosphatidylserine.

In another embodiment, the compound for use in the present invention is represented by the structure of the general formula (III):

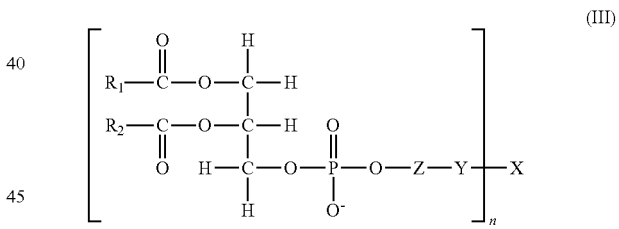

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 1 to 1000;

wherein any bond between the phosphatidyl, Z, Y and X is either an amide or an esteric bond.

In another embodiment, the compound for use in the present invention is represented by the structure of the general formula (IV):

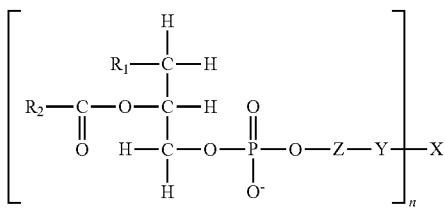

(IV)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a glycosaminoglycan; and
n is a number from 1 to 1000;
wherein any bond between the phospholipid, Z, Y and X is either an amide or an esteric bond.

In another embodiment, the compound for use in the present invention is represented by the structure of the general formula (V):

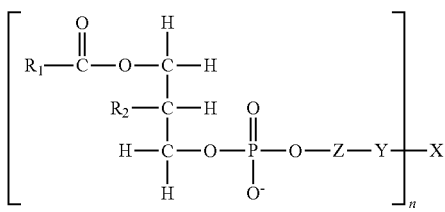

(V)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a glycosaminoglycan; and
n is a number from 1 to 1000;
wherein any bond between the phospholipid, Z, Y and X is either an amide or an esteric bond.

In another embodiment, the compound for use in the present invention is represented by the structure of the general formula (VI):

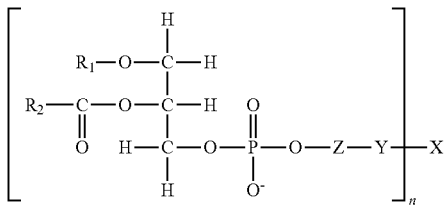

(VI)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a glycosaminoglycan; and
n is a number from 1 to 1000;
wherein any bond between the phospholipid, Z, Y and X is either an amide or an esteric bond.

In another embodiment, the compound for use in the present invention is represented by the structure of the general formula (VII):

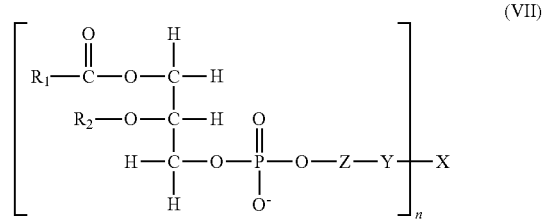

(VII)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, inositol, choline, or glycerol;
Y is either nothing or a spacer group ranging in length from 2 to 30 atoms;
X is a glycosaminoglycan; and
n is a number from 1 to 1000;
wherein any bond between the phospholipid, Z, Y and X is either an amide or an esteric bond.

In one embodiment of the invention, phosphatidylcholine (PC), phosphatidylinositol (PI), phosphatidic acid (PA), wherein Z is nothing, and phosphatidylglycerol (PG) conjugates are herein defined as compounds of the general formula (III).

In another embodiment, the compound for use in the present invention is represented by the structure of the general formula (VIII):

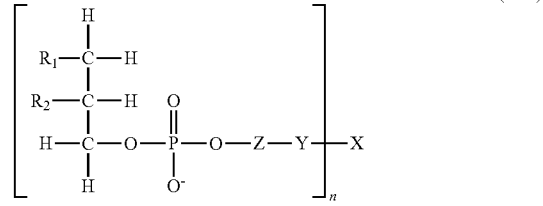

(VIII)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;
Y is either nothing or a spacer group ranging in length from 2 to 30 atoms;
X is a glycosaminoglycan; and
n is a number from 1 to 1000;
wherein any bond between the phospholipid, Z, Y and X is either an amide or an esteric bond.

In another embodiment, the compound for use in the present invention is represented by the structure of the general formula (IX):

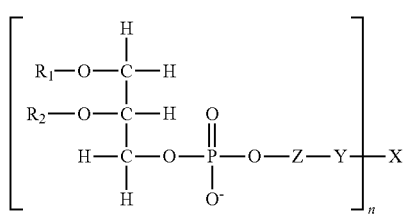

(IX)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a glycosaminoglycan; and
n is a number from 1 to 1000;
wherein any bond between the phospholipid, Z, Y and X is either an amide or an esteric bond.

In another embodiment, the compound for use in the present invention is represented by the structure of the general formula (IXa):

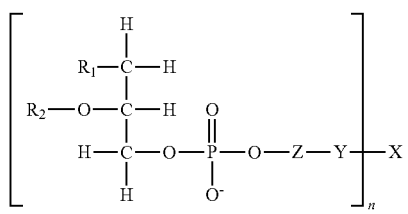

(IXa)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a glycosaminoglycan; and
n is a number from 1 to 1000;
wherein any bond between the phospholipid, Z, Y and X is either an amide or an esteric bond.

In another embodiment, the compound for use in the present invention is represented by the structure of the general formula (IXb):

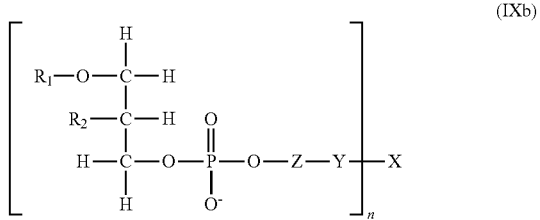

(IXb)

wherein
$R_1$ is either hydrogen or a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a glycosaminoglycan; and
n is a number from 1 to 1000;
wherein any bond between the phospholipid, Z, Y and X is either an amide or an esteric bond.

In another embodiment, the compound for use in the present invention is represented by the structure of the general formula (X):

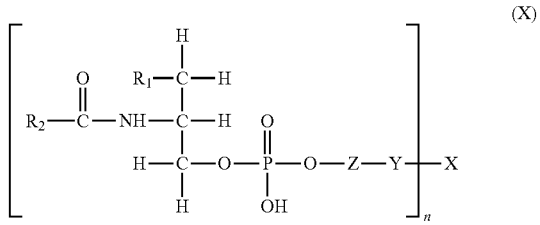

(X)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a glycosaminoglycan; and
n is a number from 1 to 1000;
wherein any bond between the ceramide phosphoryl, Z, Y and X is either an amide or an esteric bond.

In another embodiment, the compound for use in the present invention is represented by the structure of the general formula (XI):

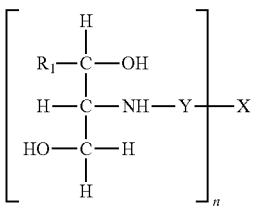
(XI)

wherein
$R_1$ is a linear, saturated, mono-unsaturated, or poly-unsaturated, alkyl chain ranging in length from 2 to 30 carbon atoms;
Y is either nothing or a spacer group ranging in length from 2 to 30 atoms;
X is a glycosaminoglycan; and
n is a number from 1 to 1000;
wherein if Y is nothing the sphingosyl is directly linked to X via an amide bond and if Y is a spacer, the spacer is directly linked to X and to the sphingosyl via an amide bond and to X via an amide or an esteric bond.

In another embodiment, the compound for use in the present invention is represented by the structure of the general formula (XII):

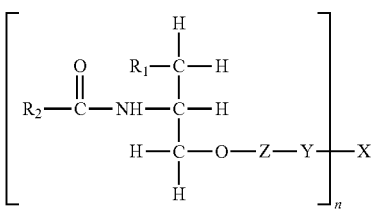
(XII)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, ethanolamine, serine, inositol, choline, or glycerol;
Y is either nothing or a spacer group ranging in length from 2 to 30 atoms;
X is a glycosaminoglycan; and
n is a number from 1 to 1000;
wherein any bond between the ceramide, Z, Y and X is either an amide or an esteric bond.

In another embodiment, the compound for use in the present invention is represented by the structure of the general formula (XIII):

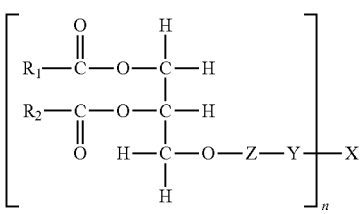
(XIII)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a glycosaminoglycan; and
n is a number from 1 to 1000;
wherein any bond between the diglyceryl, Z, Y and X is either an amide or an esteric bond.

In another embodiment, the compound for use in the present invention is represented by the structure of the general formula (XIV):

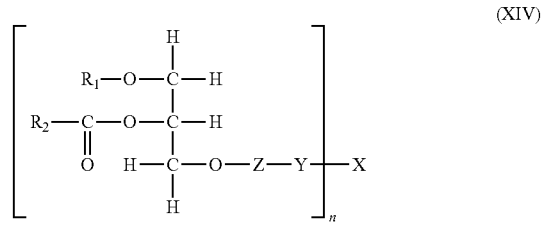
(XIV)

wherein
$R_1$ is either hydrogen or a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a glycosaminoglycan; and
n is a number from 1 to 1000;
wherein any bond between the glycerolipid, Z, Y and X is either an amide or an esteric bond.

In another embodiment, the compound for use in the present invention is represented by the structure of the general formula (XV):

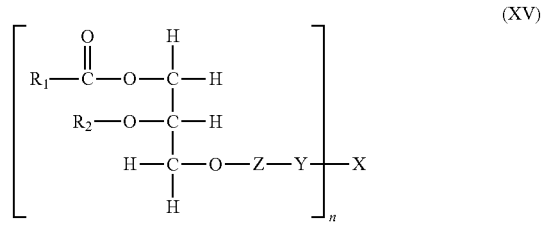
(XV)

wherein
$R_1$ is a linear, saturated, mono-unsaturated, or poly-unsaturated, alkyl chain ranging in length from 2 to 30 carbon atoms;
$R_2$ is either hydrogen or a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a glycosaminoglycan; and
n is a number from 1 to 1000;
wherein any bond between the glycerolipid, Z, Y and X is either an amide or an esteric bond.

In another embodiment, the compound for use in the present invention is represented by the structure of the general formula (XVI):

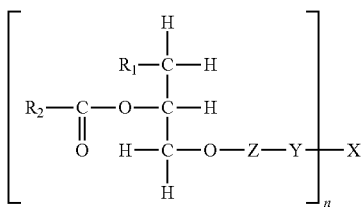

(XVI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XVII):

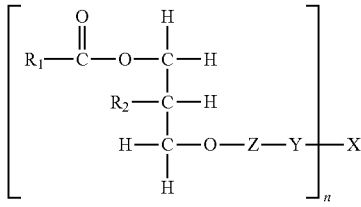

(XVII)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XVIII):

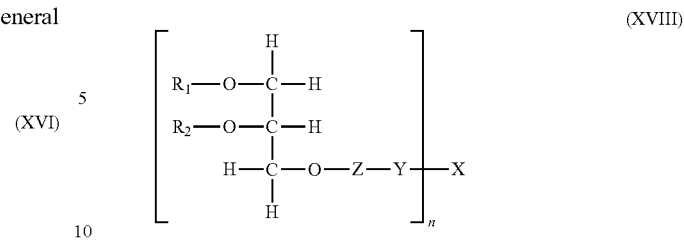

(XVIII)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XIX):

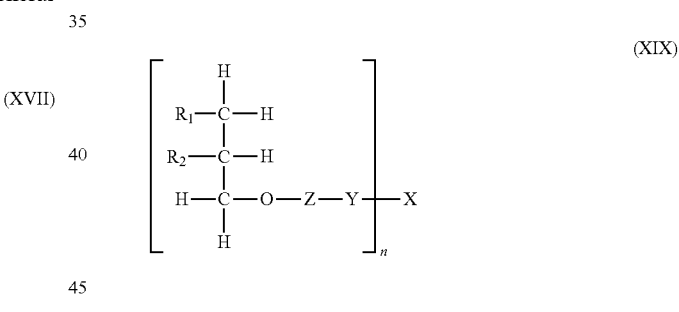

(XIX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XX):

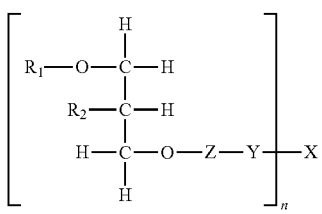

(XX)

wherein
R₁ is either hydrogen or a linear, saturated, mono-unsaturated, or poly-unsaturated, alkyl chain ranging in length from 2 to 30 carbon atoms;
R₂ is either hydrogen or a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a glycosaminoglycan; and
n is a number from 1 to 1000;
wherein any bond between the lipid, Z, Y and X is either an amide or an esteric bond.

In another embodiment, the compound for use in the present invention is represented by the structure of the general formula (XXI):

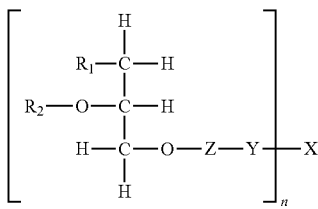

(XXI)

wherein
R₁ is either hydrogen or a linear, saturated, mono-unsaturated, or poly-unsaturated, alkyl chain ranging in length from 2 to 30 carbon atoms;
R₂ is either hydrogen or a linear, saturated, mono-unsaturated, or poly-unsaturated, alkyl chain ranging in length from 2 to 30 carbon atoms;
Z is either nothing, choline, phosphate, inositol, or glycerol;
Y is either nothing or a spacer group ranging in length from 2 to 30 atoms;
X is a glycosaminoglycan; and
n is a number from 1 to 1000;
wherein any bond between the lipid, Z, Y and X is either an amide or an esteric bond.

For any or all of the compounds represented by the structures of the general formulae (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), and (XXII) hereinabove: In one embodiment, X is a glycosaminoglycan. According to this aspect and in one embodiment, the glycosaminoglycan may be, inter alia, hyaluronic acid, heparin, heparan sulfate, chondroitin sulfate, keratin, keratan sulfate, dermatan sulfate or a derivative thereof. In another embodiment, X is not a glycosaminoglycan. In another embodiment, X is a polysaccharide, which in one embodiment is a hetero-polysaccharide, and in another embodiment, is a homo-polysaccharide. In another embodiment, X is a polypyranose.

In another embodiment, the glycosaminoglycan is a polymer of disaccharide units. In another embodiment, the number of the disaccharide units in the polymer is m. In another embodiment, m is a number from 2-10,000. In another embodiment, m is a number from 2-500. In another embodiment, m is a number from 2-1000. In another embodiment, m is a number from 50-500. In another embodiment, m is a number from 2-2000. In another embodiment, m is a number from 500-2000. In another embodiment, m is a number from 1000-2000. In another embodiment, m is a number from 2000-5000. In another embodiment, m is a number from 3000-7000. In another embodiment, m is a number from 5000-10,000. In another embodiment, a disaccharide unit of a glycosaminoglycan may be bound to one lipid or phospholipid moiety. In another embodiment, each disaccharide unit of the glycosaminoglycan may be bound to zero or one lipid or phospholipid moieties. In another embodiment, the lipid or phospholipid moieties are bound to the —COOH group of the disaccharide unit. In another embodiment, the bond between the lipid or phospholipid moiety and the disaccharide unit is an amide bond.

In another embodiment, the chondroitin sulfate may be, inter alia, chondroitin-6-sulfate, chondroitin-4-sulfate or a derivative thereof.

In one embodiment of the invention, Y is nothing. Non-limiting examples of suitable divalent groups forming the optional bridging group (which in one embodiment, is referred to as a spacer) Y, according to embodiments of the invention, are straight or branched chain alkylene, e.g., of 2 or more, preferably 4 to 30 carbon atoms, —CO-alkylen-CO, —NH-alkylene-NH—, —CO-alkylene-NH—, —NH-alkylene-NH, CO-alkylene-NH—, an amino acid, cycloalkylene, wherein alkylene in each instance, is straight or branched chain and contains 2 or more, preferably 2 to 30 atoms in the chain, —(—O—CH(CH₃)CH₂—)ₓ— wherein x is an integer of 1 or more.

According to embodiments of the invention, in addition to the traditional phospholipid structure, related derivatives for use in this invention are phospholipids modified at the C1 or C2 position to contain an amine, ether or alkyl bond instead of an ester bond. In one embodiment of the invention, the alkyl phospholipid derivatives and ether phospholipid derivatives are exemplified herein.

In one embodiment of the invention, the sugar rings of the glycosaminoglycan are intact. In another embodiment, intact refers to closed. In another embodiment, intact refers to natural. In another embodiment, intact refers to unbroken.

In one embodiment of the invention, the structure of the lipid or phospholipid in any compound according to the invention is intact. In another embodiment, the natural structure of the lipid or phospholipids in any compound according to the invention is maintained.

In one embodiment, the compounds for use in the present invention are biodegradable.

In one embodiment, the compound according to the invention is phosphatidylethanolamine bound to aspirin. In one embodiment, the compound according to the invention is phosphatidylethanolamine bound to glutarate.

In some embodiments, the compounds for use are as listed in Table 1 below.

TABLE 1

| Phospholipid | Spacer | Polymer (m.w.) | Compound |
| --- | --- | --- | --- |
| PE | None | Hyaluronic acid (2-2000 kDa) | XXII |
| Dimyristoyl-PE | None | Hyaluronic acid | XXIII |
| PE | None | Heparin (0.5-110 kDa) | XXIV |
| PE | None | Chondroitin sulfate A | XXV |
| PE | None | Carboxymethylcellulose (20-500 kDa) | XXVI |
| PE | Dicarboxylic acid + Diamine | Polygeline (haemaccel) (4-40 kDa) | XXVII |
| PE | None | Hydroxyethylstarch | XXVIII |
| PE | Dicarboxylic acid + Diamine | Dextran (1-2,000 kDa) | XXIX |
| PE | None | Aspirin | XXX |
| PE | Carboxyl amino group | Hyaluronic acid (2-2000 kDa) | XXXI |
| PE | Dicarboxyl group | Hyaluronic acid (2-2000 kDa) | XXXII |
| PE | Dipalmitoic acid | Hyaluronic acid (2-2000 kDa) | XXXIII |
| PE | Carboxyl amino group | Heparin (0.5-110 kDa) | XXXIV |
| PE | Dicarboxyl group | Heparin (0.5-110 kDa) | XXXV |
| PE | Carboxyl amino group | Chondroitin sulfate A | XXXVI |
| PE | Dicarboxyl group | Chondroitin sulfate A | XXXVII |
| PE | Carboxyl amino group | Carboxymethylcellulose (20-500 kDa) | XXXVIII |
| PE | Dicarboxyl group | Carboxymethylcellulose (20-500 kDa) | XXXIX |
| PE | None | Polygeline (haemaccel) (4-40 kDa) | XL |
| PE | Carboxyl amino group | Polygeline (haemaccel) (4-40 kDa) | XLI |
| PE | Dicarboxyl group | Polygeline (haemaccel) (4-40 kDa) | XLII |
| PE | Carboxyl amino group | Hydroxyethylstarch | XLIII |
| PE | Dicarboxyl group | Hydroxyethylstarch | XLIV |
| PE | None | Dextran (1-2,000 kDa) | XLV |
| PE | Carboxyl amino group | Dextran (1-2,000 kDa) | XLVI |
| PE | Dicarboxyl group | Dextran (1-2,000 kDa) | XLVII |
| PE | Carboxyl amino group | Aspirin | XLVIII |
| PE | Dicarboxyl group | Aspirin | XLIX |
| PE | None | Albumin | L |
| PE | None | Alginate (2-2000 kDa) | LI |
| PE | None | Polyaminoacid | LII |
| PE | None | Polyethylene glycol | LIII |
| PE | None | Lactobionic acid | LIV |
| PE | None | Acetylsalicylate | LV |
| PE | None | Cholesteryl-hemmisuccinate | LVI |
| PE | None | Maltose | LVII |
| PE | None | Cholic acid | LVIII |
| PE | None | Chondroitin sulfates | LIX |
| PE | None | Polycarboxylated polyethylene glycol | LX |
| Dipalmitoyl-PE | None | Hyaluronic acid | LXI |
| Dipalmitoyl-PE | None | Heparin | LXII |
| Dipalmitoyl-PE | None | Chondroitin sulfate A | LXIII |
| Dipalmitoyl-PE | None | Carboxymethylcellulose | LXIV |
| Dipalmitoyl-PE | None | Polygeline (haemaccel) | LXV |
| Dipalmitoyl-PE | None | Hydroxyethylstarch | LXVI |
| Dipalmitoyl-PE | None | Dextran | LXVII |
| Dipalmitoyl-PE | None | Aspirin | LXVIII |
| Dimyristoyl-PE | None | Heparin | LXVIX |
| Dimyristoyl-PE | None | Chondroitin sulfate A | LXX |
| Dimyristoyl-PE | None | Carboxymethylcellulose | LXXI |
| Dimyristoyl-PE | None | Polygeline (haemaccel) | LXXII |
| Dimyristoyl-PE | None | Hydroxyethylstarch | LXXIII |
| Dimyristoyl-PE | None | Dextran | LXXIV |
| Dimyristoyl-PE | None | Aspirin | LXXV |
| PS | None | Hyaluronic acid | LXXVI |
| PS | None | Heparin | LXXVII |
| PS | None | Polygeline (haemaccel) | LXXVIII |
| PC | None | Hyaluronic acid | LXXIX |

TABLE 1-continued

| Phospholipid | Spacer | Polymer (m.w.) | Compound |
| --- | --- | --- | --- |
| PC | None | Heparin | LXXX |
| PC | None | Polygeline (haemaccel) | LXXXI |
| PI | None | Hyaluronic acid | LXXXII |
| PI | None | Heparin | LXXXIII |
| PI | None | Polygeline (haemaccel) | LXXXIV |
| PG | None | Hyaluronic acid | LXXXV |
| PG | None | Heparin | LXXXVI |
| PG | None | Polygeline (haemaccel) | LXXXVII |
| PE | None | Glutaryl | LXXXVIII |
| Dipalmitoyl-PE | None | Alginate | LXXXIX |
| Dimyristoyl-PE | None | Alginate | XC |
| PS | None | Alginate | XCI |
| PC | None | Alginate | XCII |
| PI | None | Alginate | XCIII |
| PG | None | Alginate | XCIV |
| PS | None | Hydroxyethylstarch | XCV |
| PC | None | Hydroxyethylstarch | XCVI |
| PI | None | Hydroxyethylstarch | XCVII |
| PG | None | Hydroxyethylstarch | XCVIII |
| PE | —CO—$(CH_2)_3$—CO—NH—$(CH_2)_6$— | Hydroxyethylstarch | XCIX |
| PE | —CO—$CH_2$— | Carboxymethylcellulose | C |

In one embodiment of the invention, the compounds for use in the present invention are any one or more of Compounds I-C. In another embodiment, the invention provides a composition comprising any combination of any of the compounds of the invention or the use of any combination of any of the compounds of the invention. In another embodiment, the compounds for use in the present invention are Compound XXII, Compound XXIII, Compound XXIV, Compound XXV, Compound XXVI, Compound XXVII, Compound XXVIII, Compound XXIX, Compound XXX, Compound LI, or pharmaceutically acceptable salts thereof, in combination with a physiologically acceptable carrier or solvent. According to embodiments of the invention, these polymers, when chosen as the conjugated moiety, may vary in molecular weights from 200 to 2,000,000 Daltons. In one embodiment of the invention, the molecular weight of the polymer as referred to herein is from 200 to 1000 Daltons. In another embodiment, the molecular weight of the polymer as referred to herein is from 200 to 1000 Daltons. In another embodiment, the molecular weight of the polymer as referred to herein is from 1000 to 5000 Daltons. In another embodiment, the molecular weight of the polymer as referred to herein is from 5000 to 10,000 Daltons. In another embodiment, the molecular weight of the polymer as referred to herein is from 10,000 to 20,000 Daltons. In another embodiment, the molecular weight of the polymer as referred to herein is from 10,000 to 50,000 Daltons. In another embodiment, the molecular weight of the polymer as referred to herein is from 20,000 to 70,000 Daltons. In another embodiment, the molecular weight of the polymer as referred to herein is from 50,000 to 100,000 Daltons. In another embodiment, the molecular weight of the polymer as referred to herein is from 100,000 to 200,000 Daltons. In another embodiment, the molecular weight of the polymer as referred to herein is from 200,000 to 500,000 Daltons. In another embodiment, the molecular weight of the polymer as referred to herein is from 200,000 to 1,000,000 Daltons. In another embodiment, the molecular weight of the polymer as referred to herein is from 500,000 to 1,000,000 Daltons. In another embodiment, the molecular weight of the polymer as referred to herein is from 1,000,000 to 2,000,000 Daltons. Various molecular weight species have been shown to have the desired biological efficacy.

In one embodiment, "approximately" refers to up to 5%, 10%, 15%, 20%, or 25% of the value. In another embodiment, "approximately" refers to 5-25%, 5-15%. 10-25%, 10-20%, 15-25% of the value.

In one embodiment of this invention, low molecular weight compounds for use in the present invention are defined hereinabove as the compounds of formula (I)-(XXI) wherein X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisacharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, hyaluronic acid, glycosaminoglycan, or polypyranose.

Examples of suitable divalent groups forming the optional bridging group Y are straight- or branched-chain alkylene, e.g., of 2 or more, preferably 4 to 18 carbon atoms, —CO-alkylene-CO, —NH-alkylene-NH—, —CO-alkylene-NH—, cycloalkylene, wherein alkylene in each instance, is straight or branched chain and contains 2 or more, preferably 2 to 18 carbon atoms in the chain, —(—O—$CH(CH_3)CH_2$—)$_x$— wherein x is an integer of 1 or more.

In another embodiment, in addition to the traditional phospholipid structure, related derivatives for use in this invention are phospholipids modified at the C1 or C2 position to contain an ether or alkyl bond instead of an ester bond. These derivatives are exemplified hereinabove by the general formulae (VIII) and (IX).

In one embodiment of the invention, X is covalently conjugated to a lipid. In another embodiment, X is covalently conjugated to a lipid via an amide bond. In another embodiment, X is covalently conjugated to a lipid via an esteric bond. In another embodiment, the lipid is phosphatidylethanolamine.

In one embodiment, cell surface GAGs play a key role in protecting cells from diverse damaging agents and processes, such as reactive oxygen species and free radicals, endotoxins, cytokines, invasion promoting enzymes, and agents that induce and/or facilitate degradation of extracellular matrix and basal membrane, cell invasiveness, white cell extravasation and infiltration, chemotaxis, and others. In addition, cell surface GAGs protect cells from bacterial, viral and parasitic infection, and their stripping exposes the cell to interaction and subsequent internalization of the microorganism. Enrichment of cell surface GAGs would thus assist in protection of the cell from injurious processes. Thus, in one embodiment of the invention, PLA2 inhibitors are conjugated to GAGs or GAG-mimicking molecules. In another embodiment, these compounds for use in the present invention provide wide-range protection from diverse injurious processes, and are effective in amelioration of diseases that requires cell protection from injurious biochemical mediators.

In another embodiment, a GAG-mimicking molecule may be, inter alia, a negatively charged molecule. In another embodiment, a GAG-mimicking molecule may be, inter alia, a salicylate derivative. In another embodiment, a GAG-mimicking molecule may be, inter alia, a dicarboxylic acid.

In another embodiment, the invention provides a pharmaceutical composition for treating a subject suffering from an intestinal disease, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from an intestinal disease, including any one of the compounds for use in the present invention or any combination thereof; and a pharmaceutically acceptable carrier or excipient. In another embodiment, the compounds for use in the present invention include, inter alia, the compounds represented by the structures of the general formulae as described hereinbelow: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII), or any combination thereof.

The combination of lipids, such as, but not limited to phosphatidylethanolamine and phosphatidylserine, with additional monomer or polymer moieties, is thus a practical route to the production of new drugs for medical purposes, provided that the resultant chemical composition displays the desired range of pharmacological properties. In one embodiment, the compounds for use in the present invention possess a combination of multiple and potent pharmacological effects in addition to the ability to inhibit the extracellular form of the enzyme phospholipase A2. While the pharmacological activity of the compounds for use in the present invention described herein may be due in part to the nature of the lipid moiety, the multiple and diverse combination of pharmacological properties observed for the compounds for use in the present invention emerges from the ability of the compound structure to act essentially as several different drugs in one chemical entity.

In the cases described herein, the diversity of biological activities and the effectiveness in disease exhibited by the compounds for use in the present invention far exceed the properties anticipated by use of the starting materials themselves, when administered alone or in combination. However, the phospholipid conjugate compounds, alone or in combination, are valuable when used in the methods of treating diseases and conditions specifically described herein.

Preparation of Compounds for Use in the Present Invention

In one embodiment, the preparation of high molecular weight compounds for use in the methods of the present invention is as described in U.S. Pat. No. 5,064,817, which is incorporated fully herein by reference. In one embodiment, these synthetic methods are applicable to the preparation of low molecular weight compounds for use in the present invention as well, i.e. compounds for use in the present invention comprising monomers and dimers as the conjugated moiety, with appropriate modifications in the procedure as would be readily evident to one skilled in the art. The preparation of some low molecular weight compounds for use in the present invention may be conducted using methods well known in the art or as described in U.S. patent application Ser. No. 10/952,496, which is incorporated herein by reference in its entirety.

Without further elaboration, it is believed that one skilled in the art can, using the preceding description, utilize the present invention to its fullest extent. The following preferred specific embodiments are, therefore, to be construed as merely illustrative, and not limiting the remainder of the disclosure in any way whatsoever.

EXAMPLES

Example 1

Experimental Procedures

Animals

BALB/c male mice were used for this study and were acquired from an approved source. The mice weighed 22-25 g at the start of the study. The animals were examined for any evidence of disease. Only disease free, clinically sound, animals and animals with no history of prior use were accepted into the study. The animals were conditioned for an appropriate period of time as determined by the institution. Commercial food and drinking fluids were provided ad libitum. Maintenance of animals and experimental procedures were carried out in accordance with the NIH guidelines for the use of experimental animals. All protocols of the experiment were approved by the ethical committee of the Hebrew university (Ethical approval number MD 113.07-3), NIH approval number: OPRR-A01-5011.

Identification of Animals

Every cage was numbered and the treatment protocol was written on each cage. A unique tail mark identified each animal in every cage. Animals were assigned to the treatment groups on the basis of a random allocation.

Treatment Arms

The study design is shown below:

TABLE 1

| Treatment arms | | | | |
|---|---|---|---|---|
| Group | No. of animals | Drinking | Treatment | Compound mark |
| 1 | 8 | Water | Saline, PO, TID | S |
| 2 | 8 | 5% DSS in Water | Saline, PO, TID | S |
| 3 | 6 | 5% DSS in Water | Dexamethasone | Dex |
| 4 | 8 | 5% DSS in Water | Tami, 20 mg\ml, PO TID | A1 |
| 5 | 8 | 5% DSS in Water | MK-851, 20 mg\ml, PO TID | A2 |
| 6 | 8 | 5% DSS in Water | Tami, 5 mg\ml, PO TID | B1 |

TABLE 1-continued

| Group | No. of animals | Drinking | Treatment | Compound mark |
|---|---|---|---|---|
| 7 | 8 | 5% DSS in Water | MK-851, 5 mg\ml, PO TID | B2 |
| 8 | 8 | 5% DSS in Water | MK-827, 20 mg\ml, PO TID | C1 |
| 9 | 8 | 5% DSS in Water | MK-827, 5 mg\ml, PO TID | C2 |

PO = Orally
TID = Three Times Daily

Daily Health Observations

Animals were observed daily for general health and were weighed every other day by the technician throughout the course of the study. Animal suspected of showing any signs of pain or stress, were reported to the veterinarian performed a clinical diagnosis and treat them as necessary.

Bodyweights

Bodyweight measurements were taken from all animals at the beginning of the study and every other day.

Study Procedure

All animals were weighed and tagged according to treatment groups.

The animals were treated according to treatment arms two hours and 30 minutes before the delivering of DSS to the animals.

Water was replaced by 5% (w\v) DSS in water (except for Control group no. 1 that will receive normal tap water). A total of 150 ml of water with 5% DSS was offered to each cage. DSS was changed every 48 hours.

Treatment was administered three times on the first day, according to treatment arms, using a special gavage needle and then one time per day by gavage along with drinking water comprising the treatment compounds, because several mice died due to the frequent gavage procedure.

Dexamethasone-treated mice received 5 mg per mouse per day IP (intraperitoneal).

At the last day of the study, one hour before anesthetizing the mice, 0.2 mg of In-Fn per mouse was administered orally for permeability measurements.

Necropsy

At the end of the experiment (Day 7), animals were anesthetized using a Xylazine-ketamine solution and terminal bleeding was conducted from the heart. Blood was delivered for cytokines analysis and quantification of In-Fn in the blood. The colon was taken out, measured and evaluated grossly, placed into appropriately labeled formalin containers.

Mesenteric Lymph-nodes were harvested into saline containers for cytokines evaluation.

Histology and Histological Evaluation

Immediately after dissection, the colon was placed in 10% phosphate buffered formalin (at least ten-fold volume) for at least 48 hours and transferred for histological processing.

The specimens were dehydrated through an ethanol series and paraffin embedded. The specimens were sectioned to 5-10 μm. The sections will be stained with H&E for histological analysis.

Statistical Analysis

Results were expressed as means±SE. The significance of differences was assessed by the 1-way ANOVA test. p values<0.05 were considered statistically significant.

Example 2

Lipid-Conjugates Prevent Decreased Body Weight in an Animal Model of IBD

Mice exposed to 5% DSS developed symptoms of acute colitis, with diarrhea and severe weight loss. Shortening of the colon was observed upon removal.

Body weights decreased in groups drinking DSS and receiving saline (control), and increased in groups drinking water or in groups drinking DSS and receiving 5 mg/ml of Compound XXII (Tami 5 mg\ml, MK-851 5 mg\ml, and MK-827 5 mg\ml).

In the control mice, colon length was significantly decreased 7 days after DSS administration (72.00±2.60 and 91.14±2.07 in the DSS and water groups respectively). However, a trend for reversal of decreased colon length after DSS administration was seen in the group treated with 5 mg\ml of Compound XXII (Table 2).

TABLE 2

Data sorted by test article (Mean ± SE. Dev)

|  | % Change in body weight | Colon length (mm) |
|---|---|---|
| Water | 1.91 ± 2.24 | 91.14 ± 2.07 |
| DSS | −11.75 ± 3.56 | 72.00 ± 2.60 |
| 5% DSS w Tami 5 mg\ml | 1.77 ± 3.23 | 81.85 ± 2.11 |
| 5% DSS w MK-851 5 mg\ml | 2.24 ± 1.62 | 81.83 ± 2.34 |
| 5% DSS w MK-827 5 mg\ml | 0.14 ± 1.33 | 75.62 ± 1.77 |

The present study demonstrates that the treatment with the PLA2 derivatives in the lower concentration ameliorated the colonic mucosal injury induced by DSS in mice as shown by the weight change.

What is claimed is:

1. A method for the therapeutic treatment of an intestinal disease or disorder in a subject suffering from said intestinal disease or disorder, comprising administering to the subject suffering from said intestinal disease or disorder a composition comprising a compound represented by the structure of the formula:

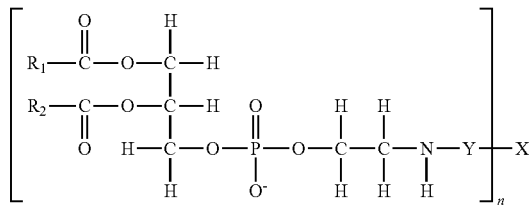
(I)

wherein
$R_1$ and $R_2$ each is palmitoyl or myristoyl;
Y is nothing;
X is a hyaluronic acid; and
n is a number from 1 to 1000,
wherein said intestinal disease or disorder is an inflammatory bowel disease selected from the group consisting of Crohn's Disease and ulcerative colitis.

2. A method for the therapeutic treatment of an intestinal disease or disorder in a subject suffering from said intestinal disease or disorder, comprising administering to the subject suffering from said intestinal disease or disorder a composition comprising a compound represented by the structure of the formula:

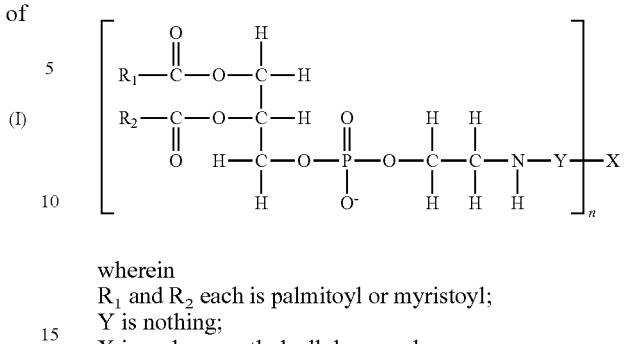
(I)

wherein
$R_1$ and $R_2$ each is palmitoyl or myristoyl;
Y is nothing;
X is carboxymethylcellulose; and
n is a number from 1 to 1000,
wherein said intestinal disease or disorder is an inflammatory bowel disease selected from the group consisting of Crohn's Disease and ulcerative colitis.

3. The method of claim 1 or 2, wherein said compound comprises dipalmitoyl phosphatidylethanolamine or dimyristoyl phosphatidylethanolamine.

4. The method of claim 1 or 2, wherein said inflammatory bowel disease is Crohn's Disease.

5. The method of claim 1 or 2, wherein said inflammatory bowel disease is ulcerative colitis.

6. The method of claim 1 or 2, wherein said compound is administered at a dose of 5 mg/ml.

7. The method of claim 1 or 2, wherein said compound is administered at a dose of 20 mg/ml.

* * * * *